US00PP31431P2

(12) United States Plant Patent
Hansen

(10) Patent No.: US PP31,431 P2
(45) Date of Patent: Feb. 4, 2020

(54) *AGAPANTHUS* PLANT NAMED 'GALAXY WHITE'

(50) Latin Name: ***Agapanthus praecox* (L.) hybrid**
Varietal Denomination: Galaxy White

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,793

(22) Filed: Jan. 14, 2019

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./263.1, 398
See application file for complete search history.

*Primary Examiner* — Susan McCormick Ewoldt
*Assistant Examiner* — Karen M Redden

(57) ABSTRACT

A new and distinct *Agapanthus* plant named 'Galaxy White' characterized by winter-hardy compact habit with clean, lanceolate, medium-green foliage that goes dormant in the winter; single white flowers on tall scapes flowering beginning about mid-July and with repeating new scapes into late summer for about six weeks.

1 Drawing Sheet

Botanical classification: *Agapanthus praecox* (L.) hybrid.
Variety denomination: 'Galaxy White'.

STATEMENT REGARDING PRIOR DISCLOSURES UNDER 37 CFR 1.77(B)(6)

The first public disclosure of the claimed plant, in the form of a website to the public and email release to customers, was made by Walters Gardens, Inc. on Feb. 1, 2018. Walters Gardens, Inc. obtained the new plant and information about the new plant directly from the inventor. No plants of *Agapanthus* 'Galaxy White' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct Lily of the Nile plant, *Agapanthus* 'Galaxy White' hereinafter also referred to as the new plant or just the cultivar name, 'Galaxy White'. *Agapanthus* 'Galaxy White' was selected by the inventor in July of 2012 in the research fields of a wholesale perennial nursery in Zeeland, Mich., USA. The new plant originated from the controlled cross between the female or seed parent known as 'Old Wayside Gardens Clone' (not patented) and 'Kingston Blue' (not patented) as the male or pollen parent. The new plant was selected as a single seedling from this cross and was assigned the breeder code H10-04-01 during the remainder of the trial process.

The new plant has been asexually propagated by division and shoot tip tissue culture at the same wholesale nursery in Zeeland, Mich. since 2012 with all resultant asexually propagated plants having retained all the same unique traits as the original plant. *Agapanthus* 'Galaxy White' has proven to be stable and reproduces true to type in successive generations of asexual reproduction.

The most similar known lily of the Nile cultivars are: 'Pavlova' U.S. Plant Pat. No. 23,542, 'Snow Pixie' U.S. Plant Pat. No. 15,470, 'White Heaven' (not patented), 'Prolific White' (not patented) and 'WP001' U.S. Plant Pat. No. 27,357. 'Pavlova' and 'Snow Pixie' are shorter in flower with fewer flowers per stem and less winter-hardy than the new plant. 'Snowstorm' (not patented) is also shorter in flower with fewer flowers, but hardiness has not been compared. 'White Heaven' is slightly shorter in flower, has larger flowers and larger flower heads, and the foliage is wider and is also much less winter-hardy. 'Prolific White' has slight dark purple pigment near the top of the flower stems and is equally as hardy. 'WP001' is much shorter but hardiness has not been compared.

The female plant has a light blue flower with fewer flowers per umbel. 'Kingston Blue' has blue flowers with fewer flower per stem, flowering height is shorter and not as winter-hardy as the new plant.

*Agapanthus* 'Galaxy White' differs from all other lily of the Nile plants known to the applicant, by the combination of the following traits:

1. White flowers in large heads on tall, stiff stems;
2. Long season of bloom.
3. Winter-hardy, compact, clean, medium-green foliage that goes dormant in the winter;
4. Flowering begins about mid-July with excellent coverage and sending new scapes into late summer for about six weeks;

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
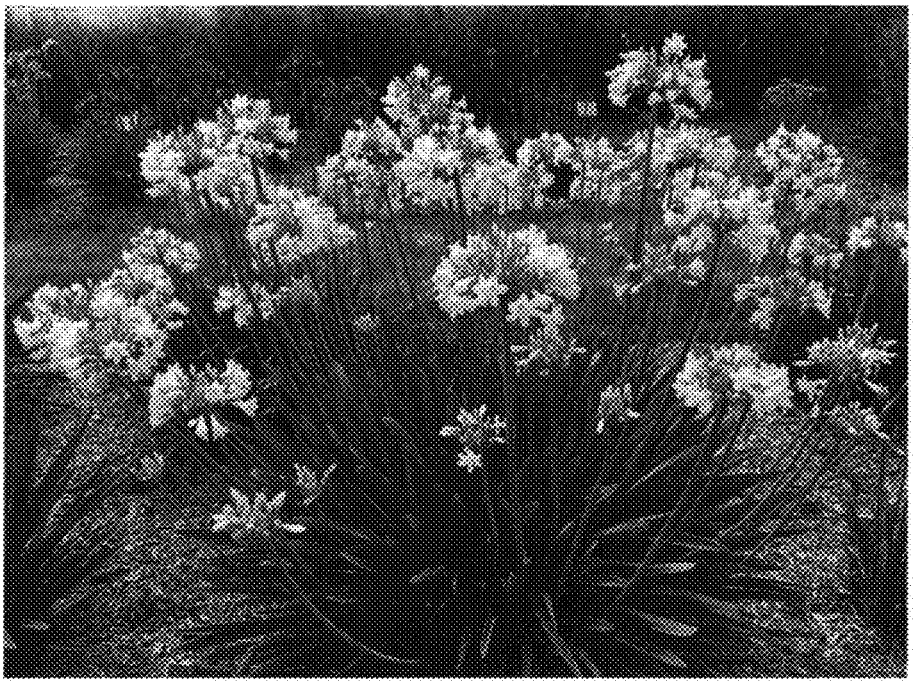
FIG. 1 shows an eight-year-old plant in peak flower during mid-summer in a full-sun research garden in Zeeland, Mich.
Figure 2:
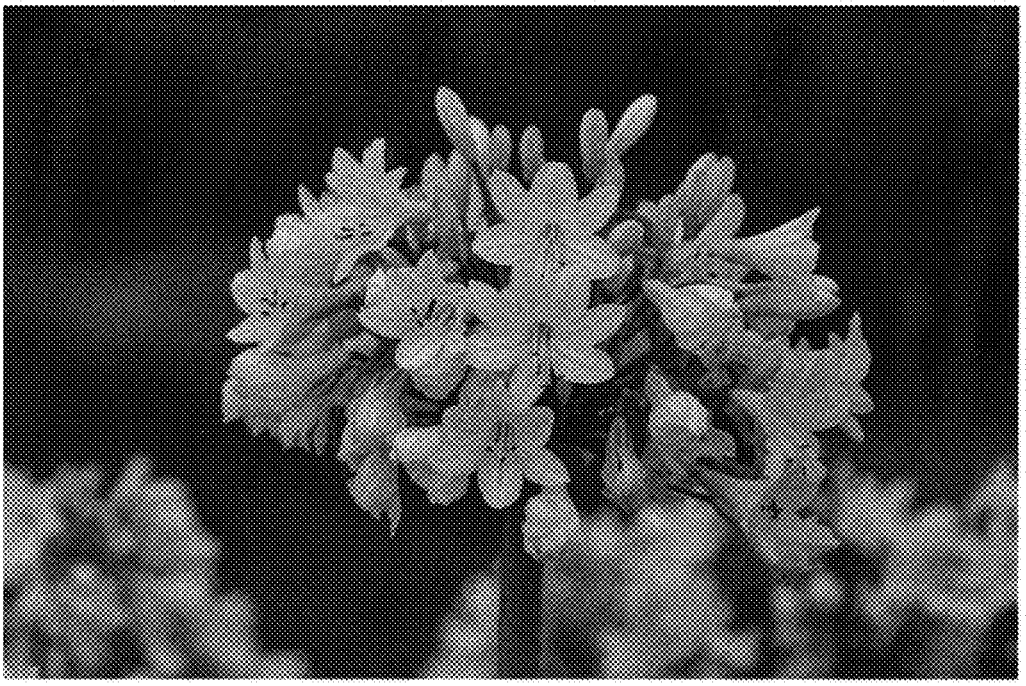
FIG. 2 shows a close-up of the flower and buds.

The following descriptions and color references are based on the 2015 edition of The Royal Horticultural Society Colour Chart except where common dictionary terms are used. The new plant, *Agapanthus* 'Galaxy White', has not been observed under all possible environments. The phenotype may vary slightly with different environmental conditions, such as temperature, light, fertility, moisture and maturity levels, but without any change in the genotype. The following observations and size descriptions are of an eight-year-old plant in a sunny landscape at a research garden in Zeeland, Mich. with and supplemental water and fertilizer.

Botanical classification: *Agapanthus praecox* (L.) hybrid;

Parentage: Female (seed) parent is known only as 'Old Wayside Gardens Clone'; male (pollen) parent is 'Kingston Blue';

Propagation: Division of the rhizome and shoot tip tissue culture;

Growth rate: Moderate to rapid;

Crop time: About 10 to 14 weeks to flower starting in spring in a 3.8 liter container from vernalized one-year-old plant;

Rooting habit: Primary roots thick and fleshy, secondary roots fibrous;

Root color: Nearest RHS 159C depending on soil type;

Plant shape and habit: Winter-hardy herbaceous perennial with pseudo-umbel inflorescence; about 50 flowering stems surrounded by acaulescent foliage forming a dense mound;

Plant size: Foliage width about 82.5 cm wide, height about 40.0 cm tall from soil line to the top of the leaves; about 110.0 cm tall to highest inflorescence and about 90.0 cm wide at the widest point at the top of the inflorescences;

Leaves: Linear; acaulescent; bi-ranked; entire; glabrous and glaucous both abaxial and adaxial; sessile; apex acute, base sheathing scape; to about 37.5 cm long and 11.0 mm across, average about 35.0 cm long and about 10.0 mm across; about 12 per division; attitude upright becoming outright and arching;

Leaf color: Abaxial and adaxial base nearest RHS 144D; mature and young adaxial and abaxial nearest RHS 137A;

Veins: Parallel; abaxial midrib about 2.0 mm across and color same as surrounding leaf tissue;

Inflorescence: Pseudo-umbel initially sheathed in two bracts;

Bracts: Deltoid; dehiscent; acuminate apex; truncate base; scarious; to about 45.0 mm long and 15.0 mm wide near middle;

Bract color: Variable; nearest RHS 165D and RHS 165B;

Flowers: Funnelform; single, with two sets of three tepals; about 65 to 80 per scape; upward and outwardly facing; about 30.0 mm across and 26.0 mm deep; individually lasting for about four to five days, individual inflorescence lasting about two weeks; flowers remain effective from late-July repeating into late August for approximately six weeks in Zeeland, Mich.;

Flower fragrance: None detected;

Buds one to two days prior to opening: Ellipsoidal with rounded apex and base; about 18.0 mm long and about 7.0 mm in diameter at widest point with near apex;

Bud color one day from opening: Proximal 4.0 mm nearest RHS 150D, distally nearest RHS NN155D;

Tepals: 2 sets of 3; both sets open to almost flat face; both sets identical in coloration;

Inner tepals: Glabrous; obtuse; rounded apex; base attenuate, fused in proximal 8.0 mm; margin entire to microerose; width at base about 2.0 mm; about 10.0 mm across at widest point and about 23.0 mm long;

Outer tepals: Glabrous; obtuse; rounded apex; base attenuate, fused in proximal 8.0 mm; margin entire; width at base about 2.0 mm; about 6.0 mm across at widest point and about 23.0. m long;

Tepal color adaxial: Distally nearest RHS NN155D, base nearest RHS 4D;

Tepal color abaxial: Distally nearest RHS NN155D; basal 5.5 mm nearest RHS 157B; rarely with slight lavender blush near apex of nearest RHS 92D;

Pedicel: Cylindrical; average about 36.0 mm long and 1.0 mm diameter; upright to outright;

Pedicel color: Between RHS 144A and RHS 146C distally blushed with nearest RHS 187A;

Peduncle: Becoming cylindrical in maturity; typically one per division; erect; to about 110.0 cm tall and 11.0 mm diameter at base, average 96.0 cm tall; extending above foliage;

Peduncle color: Between RHS 146D and RHS 144A proximally;

Gynoecium: Single; tricarpelled; about 22.0 mm long;

*Style*.—Single, arcuate upwards in distal one-third; about 13.0 mm long, 0.5 mm diameter; color nearest RHS NN155D.

*Stigma*.—About 0.3 mm across; color nearest RHS NN155C.

*Ovary*.—Superior; ellipsoidal; about 8.5 mm long and 3.5 mm diameter near middle with an acute apex and truncate base; color nearest RHS 145C.

Androecium: Six;

*Filaments*.—Six; adnate to inner corolla in proximal 6.0 mm and free in distal 11.0 mm; about 0.5 mm in diameter; arcuate slightly upward; color nearest RHS NN155D.

*Anthers*.—Oblong; dorsifixed, longitudinal; about 3.0 mm long and 1.0 mm wide; color closest to RHS N92D.

*Pollen*.—Color nearest RHS 11B.

Fruit: Oblong ellipsoidal; non-fleshy, dehiscent, tri-loculicidal capsule with three distinct lobes; about 21.0 mm long and 9.0 mm in across; color while maturing nearest RHS N144D and at dehiscence variable between RHS 164D and RHS 166B at lines of dehiscence;

Seed: Up to about 30 per capsule; flattened single wing with embryo situated near one end; about 6.0 mm long, about 3.0 mm wide and about 1.0 mm thick at embryo; color nearest RHS 202A;

Disease and pest resistance and tolerance: 'Galaxy White' has not shown resistance to diseases and pests beyond that common for lily of the Nile plants. The plant grows best and shows best coloration with plenty of moisture, adequate drainage, but is able to tolerate some drought when mature and direct sun without leaf burn when provided sufficient water.

Hardiness at least from USDA zone 6 through 11. The new plant is useful for landscaping en masse, as a single specimen or small groups, as a container plant and as a cut flower.

The invention claimed is:

1. A new and distinct ornamental plant cultivar named *Agapanthus* 'Galaxy White' as herein described and illustrated.

* * * * *